US00PP25645P2

(12) United States Plant Patent
Nishikawa

(10) Patent No.: US PP25,645 P2
(45) Date of Patent: Jun. 23, 2015

(54) ***DELOSPERMA* PLANT NAMED 'WOWDAY2'**

(50) Latin Name: *Delosperma cooperi*
Varietal Denomination: WOWDAY2

(71) Applicant: Koichiro Nishikawa, Katuta-gun (JP)

(72) Inventor: Koichiro Nishikawa, Katuta-gun (JP)

( * ) Notice: Subject to any disclaimer, the term of this patent is extended or adjusted under 35 U.S.C. 154(b) by 180 days.

(21) Appl. No.: 13/987,587

(22) Filed: Aug. 9, 2013

(51) Int. Cl.
*A01H 5/00* (2006.01)

(52) U.S. Cl.
USPC ..... Plt./422

(58) Field of Classification Search
USPC ..... Plt./422
See application file for complete search history.

*Primary Examiner* — Annette Para
(74) *Attorney, Agent, or Firm* — Penny J. Aguirre

(57) ABSTRACT

A new cultivar of *Delosperma* plant, 'WOWDAY2', characterized by its compact and very horizontal plant habit, its very floriferous and long blooming flowering habit, and its large flowers with petals that are red on the outer region and yellow towards the center of the flower surrounding yellow petaloids.

2 Drawing Sheets

Botanical classification: *Delosperma cooperi.*
Variety denomination: 'WOWDAY2'.

CROSS REFERENCE TO RELATED APPLICATIONS

This application is co-pending with U.S. Plant Patent Applications filed for plants derived from the same breeding program that are entitled *Delosperma* Plant Named 'WOWDOY3' (U.S. Plant patent application Ser. No. 13/987,585), *Delosperma* Plant Named 'WOW2011-1' (U.S. Plant patent application Ser. No. 13/987,575), *Delosperma* Plant Named 'WOWDRY1' (U.S. Plant patent application Ser. No. 13/987,588), *Delosperma* Plant Named 'WOWDRW5' (U.S. Plant patent application Ser. No. 13/987,584), and *Delosperma* Plant Named 'WOWDW7' (U.S. Plant patent application Ser. No. 13/987,577).

BACKGROUND OF THE INVENTION

The present invention relates to a new and distinct cultivar of *Delosperma* plant, botanically known as *Delosperma cooperi* 'WOWDAY2' and will be referred to hereinafter by its cultivar name, 'WOWDAY2'. The new cultivar of *Delosperma* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with low-growing and well-spreading growth habits combined with long flowering periods and a unique range of flower colors.

'WOWDAY2' was selected in the Inventor's trial garden in summer of 2011 as a single unique plant from amongst the seedlings derived from self crossing an unnamed plant from the Inventor's breeding program, ref. code HANADAY 1003, in summer of 2010.

Asexual propagation of the new cultivar was first accomplished by softwood stem cuttings in summer of 2011 by the Inventor in Katsuta-Gun, Okayama-Pref., Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'WOWDAY2' as a unique cultivar of *Delosperma.*

1. 'WOWDAY2' exhibits a compact and horizontal plant habit.
2. 'WOWDAY2' exhibits a very floriferous and long blooming flowering habit; blooming about 8 months.
3. 'WOWDAY2' exhibits large flowers with petals that are red on the outer region and yellow towards the center of the flower surrounding yellow petaloids.

The parent plant of 'WOWDAY2', ref. code HANADAY 1003, differs from 'WOWDAY2' in having a taller plant habit and in blooming for a shorter time period. 'WOWDAY2' can be most closely compared to the cultivar 'Jewel of Desert Garnet' (U.S. Plant Pat. No. 23,471), which is similar to 'WOWDAY2' in having a horizontal plant habit and red coloration to the petals. 'Jewel of Desert Garnet' differs from 'WOWDAY2' in having smaller flowers that have pink on the lower portion of the petals and pink petaloids, in having a shorter bloom period, and in having a shorter plant height. 'WOWDAY2' can also be compared to cultivars with co-pending patent applications from the same breeding program, which are similar in plant height and in having large flowers.

'WOWDRY1' has flowers with petals that are magenta pink on the outer region and yellow and white towards the center of the flower surrounding yellow and white petaloids.

'WOW2011-1' has flowers with yellow petals and yellow-green petaloids.

'WOWDRW5' has flowers with petals that are magenta pink on the outer region and white towards the center of the flower surrounding white petaloids.

'WOWDW7' has flowers with white petals and white petaloids.

'WOWDOY3' has flowers with petals that are orange on the outer region and yellow towards the center of the flower surrounding yellow petaloids.

BRIEF DESCRIPTION OF THE DRAWINGS

The accompanying colored photographs illustrate the overall appearance and distinct characteristics of the new *Delosperma*. The plant in the photograph is 3 months in age as grown in a 9-cm container in an unheated greenhouse in Noordwijkerhout, The Netherlands.

The photograph in FIG. 1 provides a side view of 'WOWDAY2' in bloom.

Figure 1:
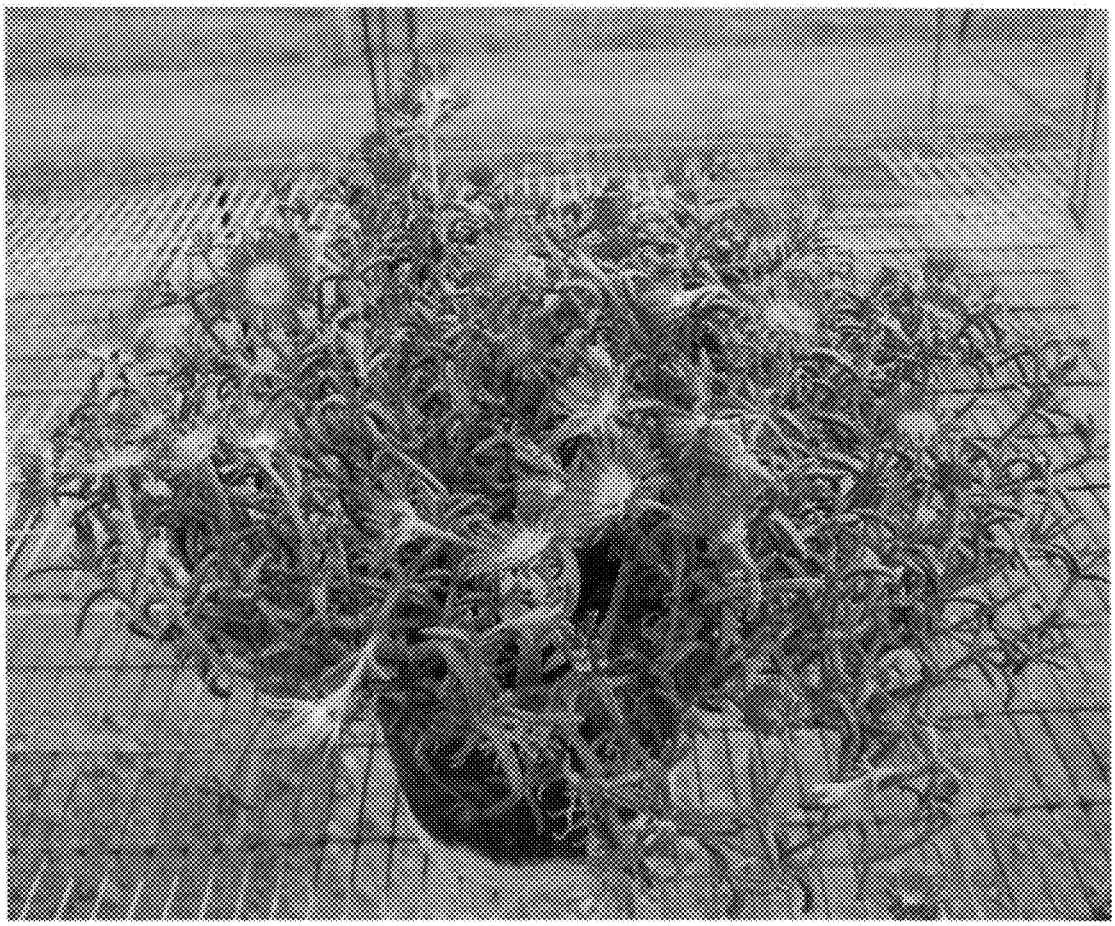
Figure 2:
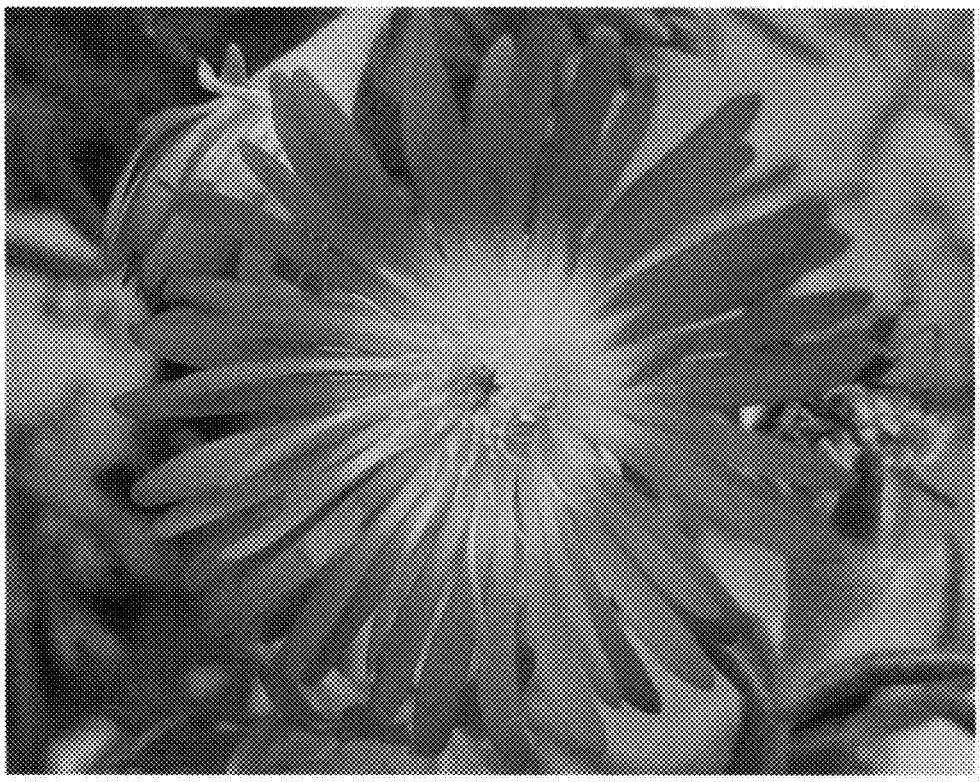

The photograph in FIG. 2 provides a close-up view of a flower of 'WOWDAY2'.

Figure 3:
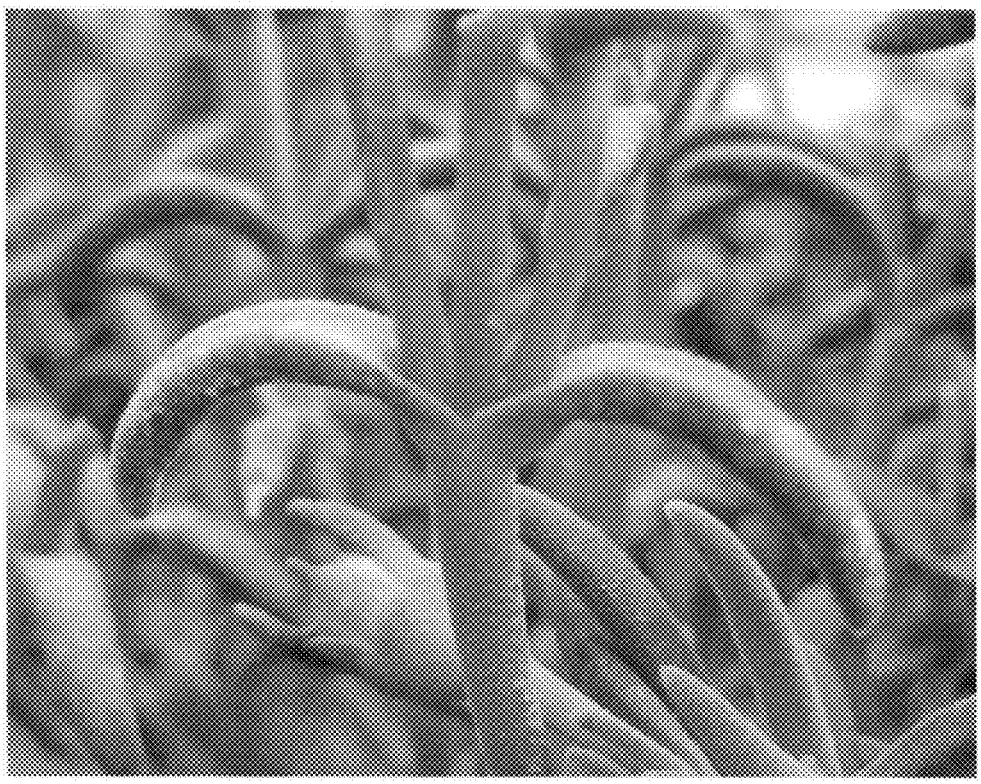

The photograph in FIG. 3 provides a close-up view of the foliage of 'WOWDAY2'.

The colors in the photograph may differ slightly from the color values cited in the detailed botanical description, which accurately describe the colors of the new *Delosperma*.

DETAILED BOTANICAL DESCRIPTION

The following is a detailed description of 3 months-old plants of the new cultivar as grown in 9-cm containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from spring through fall for 8 months in The Netherlands.

*Plant type.*—Herbaceous perennial.

*Plant habit.*—Flattened, prostrate.

*Height and spread.*—Reaches an average of 10 cm in height and about 24.1 cm in diameter.

*Cold hardiness.*—Observed to be hardy to at least U.S.D.A. Zone 7.

*Diseases.*—No more susceptible to diseases than other *Delosperma cooperi* varieties.

*Root description.*—Fibrous roots.

*Propagation.*—Softwood stem cuttings.

*Growth habit.*—Moderate.

Stem description:

*Shape.*—Round.

*Stem color.*—Young stems; 145C upper side strongly tinged with 182B, older stems 196C to 196D.

*Stem size.*—Lateral branches; an average of 10 cm in length and 2.5 mm in diameter.

*Internode length.*—An average of 2.3 mm.

*Stem substance.*—Succulent.

*Stem surface.*—Moderately glossy, moderately pubescent with very short glandular hairs; an average of 0.2 mm in length and closest to 155C in color.

*Branching habit.*—Freely branching both basal and lateral, an average of 14 lateral branches per stem.

Foliage description:

*Leaf shape.*—Ligulate, triangular in diameter.

*Leaf substance.*—Succulent.

*Leaf division.*—Simple.

*Leaf base.*—Cuneate.

*Leaf apex.*—Acute.

*Leaf venation.*—No veins visible.

*Leaf margins.*—Entire.

*Leaf arrangement.*—Opposite.

*Leaf surface* (*upper and lower surface*).—Slightly glossy, sparsely to moderately pubescent with very short glandular hairs; an average of 0.2 mm in length, 157D in color.

*Leaf color.*—Young upper and lower surface; 138B, mature upper surface 137B and lower surface; 137C.

*Leaf size.*—About 3.0 cm in length and 4 mm in width.

*Leaf quantity.*—Average of 12 (6 pairs) per lateral branch.

*Leaf attachment.*—Sessile.

Inflorescence description:

*Inflorescence type.*—Flowers solitary, terminal.

*Flower number.*—An average of 1 per lateral stem, 77 per plant in a 9-cm container.

*Flower fragrance.*—Faint, sweet and pleasant.

*Flower aspect.*—Outward to upright.

*Flower longevity.*—A few days, self-cleaning.

*Flower type.*—Single.

*Flower size.*—Average of 3.3 cm in diameter and 1.3 cm in depth.

*Flower buds.*—Broadly ovate to oblong in shape, an average of 1 cm in length and 5 mm in diameter, color; 138A with sepal portion 145B.

*Calyx.*—Rotate in shape, average of 5 mm in depth and 1.5 cm in diameter.

*Sepals.*—5, rotate, ovate in shape, margin entire, an average of 7 mm in length and 3 mm in width, broadly acute apex, broadly cuneate base, surface is smooth and dull, color young upper and lower surface; 138A, base 145B, color mature upper and lower surface; 143B to 143C.

*Petals.*—An average of 40 per flower, rotate and slightly curved downward, narrowly oblanceolate in shape, surface is smooth and glossy on both surfaces, margin entire, apex obtuse, base cuneate, an average of 1.5 cm in length and 1.5 mm in width, color; opening flowers upper surface; 42B, base 13B, opening flowers lower surface; 45C, base 13B to 14B, fully opened flower upper surface; 42B, base 13B, fully opened flower lower surface; 45C, base a blend between 13B to 14B.

*Petaloids.*—An average of 30 per flower, rotate and near vertical surrounding stamens, lanceolate in shape, moderately to highly glossy on both surfaces, margin entire, apex obtuse, base truncate, an average of 6 mm in length and 0.75 mm in width, color immature and mature upper and lower surface; 5D with very base NN155C to NN155D.

*Peduncle.*—Average of 1.9 cm in length and 1.5 mm in diameter, straight on top of lateral branch at 0°, color; a blend between 144B and 145C, surface moderately glossy, sparsely to moderately pubescent with very short glandular hairs.

*Pedicel.*—None.

Reproductive organs:

*Pistils.*—About 5, an average of 2 mm in length, stigma triangular shaped, style and stigma (not distinguishable) and combined an average of 2 mm in length and 151B in color, ovary is 143C in color.

*Stamens.*—Average 60, 12A in color, anthers are dorsifixed and narrowly oblong in shape, an average of 0.5 mm in diameter, filaments are 4 mm in length NN155D in color, anthers are NN155D in color, pollen is moderate to high in quantity and 6A in color.

*Fruit*.—Fruit and seed production was not observed under the conditions tested.

It is claimed:

1. A new and distinct variety of *Delosperma* plant named 'WOWDAY2' as described and illustrated herein.

* * * * *